United States Patent [19]

Zdeb et al.

[11] Patent Number: 4,936,829
[45] Date of Patent: Jun. 26, 1990

[54] DRUG DELIVERY APPARATUS INCLUDING BENEFICIAL AGENT CHAMBER WITH CHIMNEY FOR A DIRECTED FLOW PATH

[75] Inventors: Brian D. Zdeb, Round Lake Park; William E. Younkes, Libertyville; Thomas J. Roeser, Barrington, all of Ill.

[73] Assignee: Baxter International Inc., Deerfield, Ill.

[21] Appl. No.: 262,210

[22] Filed: Oct. 19, 1988

[51] Int. Cl.5 ............................................. A61M 5/14
[52] U.S. Cl. ....................................... 604/85; 604/86; 604/406
[58] Field of Search ....................... 604/82–92, 604/413, 416, 406, 56, 410–412, 414, 415; 222/83, 211, 479, 564

[56] References Cited

U.S. PATENT DOCUMENTS

| 2,612,160 | 9/1952 | Barr | 604/406 |
| 3,208,639 | 9/1965 | Marwell et al. | 222/83 |
| 3,993,066 | 11/1976 | Virag | 604/56 |
| 4,296,786 | 10/1981 | Brignola | 604/416 |
| 4,317,525 | 3/1982 | Schuessler et al. | 604/403 |
| 4,325,368 | 4/1982 | Kaemmerer | 604/82 |
| 4,410,321 | 10/1983 | Pearson et al. | 604/56 |
| 4,515,585 | 5/1985 | Urquhart et al. | 604/85 |
| 4,552,555 | 11/1985 | Theeuwes | 604/85 |
| 4,581,016 | 4/1986 | Gettig | 604/88 |
| 4,589,867 | 5/1986 | Israel | 604/85 |
| 4,614,437 | 9/1986 | Buehler | 604/88 |
| 4,832,690 | 5/1989 | Kuu | 604/83 |

FOREIGN PATENT DOCUMENTS

| 0966701 | 9/1957 | Fed. Rep. of Germany | 604/406 |
| 2006010 | 12/1969 | France | 604/82 |
| 8603417 | 6/1986 | PCT Int'l Appl. | 604/82 |
| 8707158 | 12/1987 | PCT Int'l Appl. | 604/413 |
| 884078 | 12/1961 | United Kingdom | 604/416 |

Primary Examiner—Stephen C. Pellegrino
Assistant Examiner—Ralph Lewis
Attorney, Agent, or Firm—Paul E. Schaafsma; Bradford R. L. Price; Paul C. Flattery

[57] ABSTRACT

A cartridge for introducing a beneficial agent into a medical fluid conduit is disclosed. The cartridge includes a pierceable stopper having a hollow, open ended protrusion extending into the cartridge chamber and having the beneficial agent retained therein by a liquid pervious barrier. The hollow, open ended protrusion creates a directed flow path within the cartridge.

13 Claims, 11 Drawing Sheets

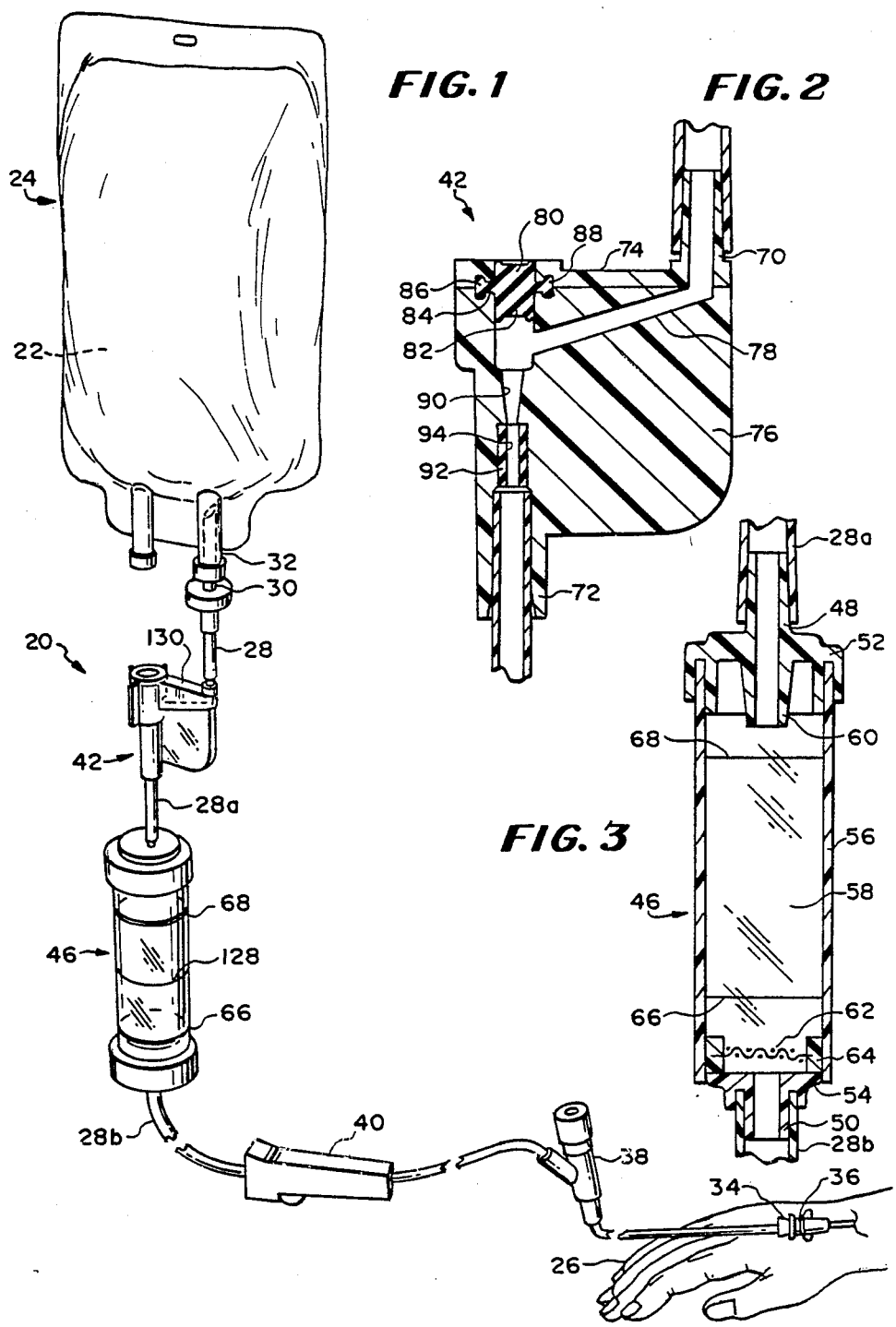

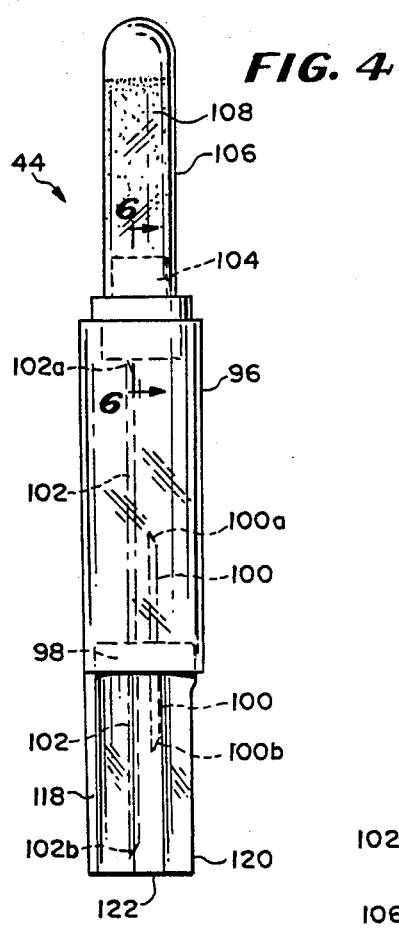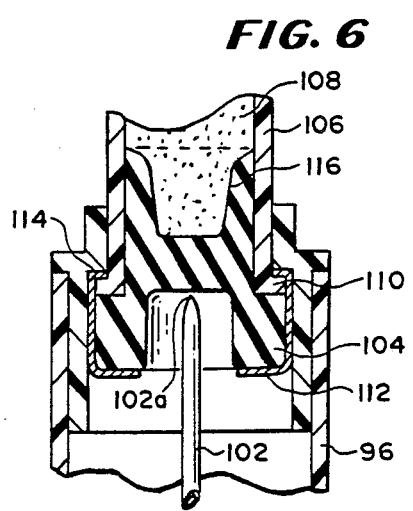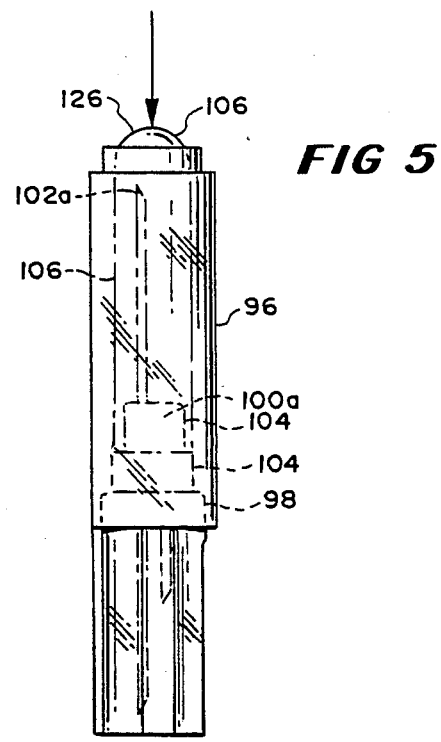

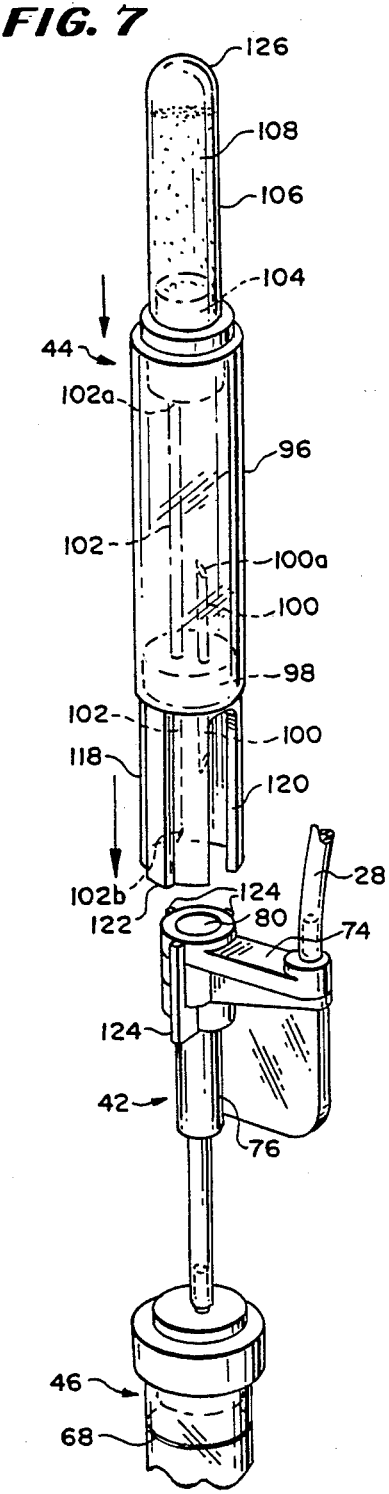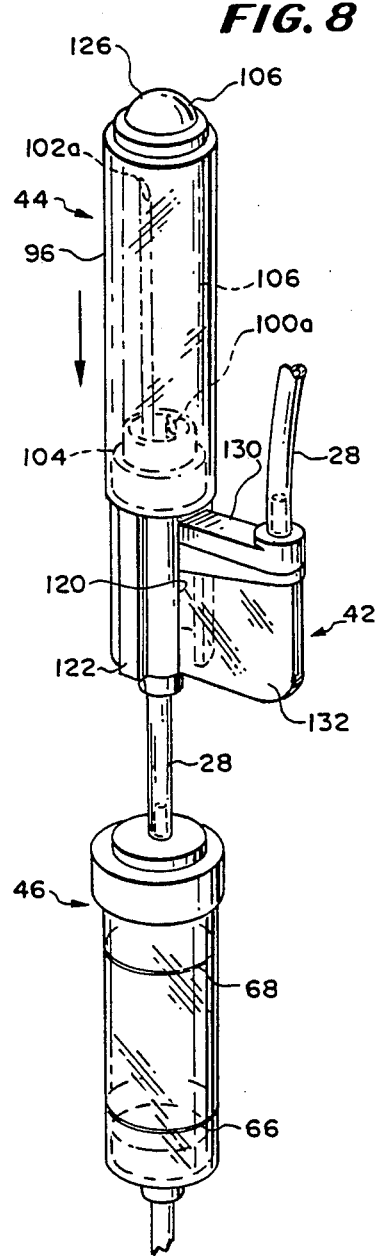

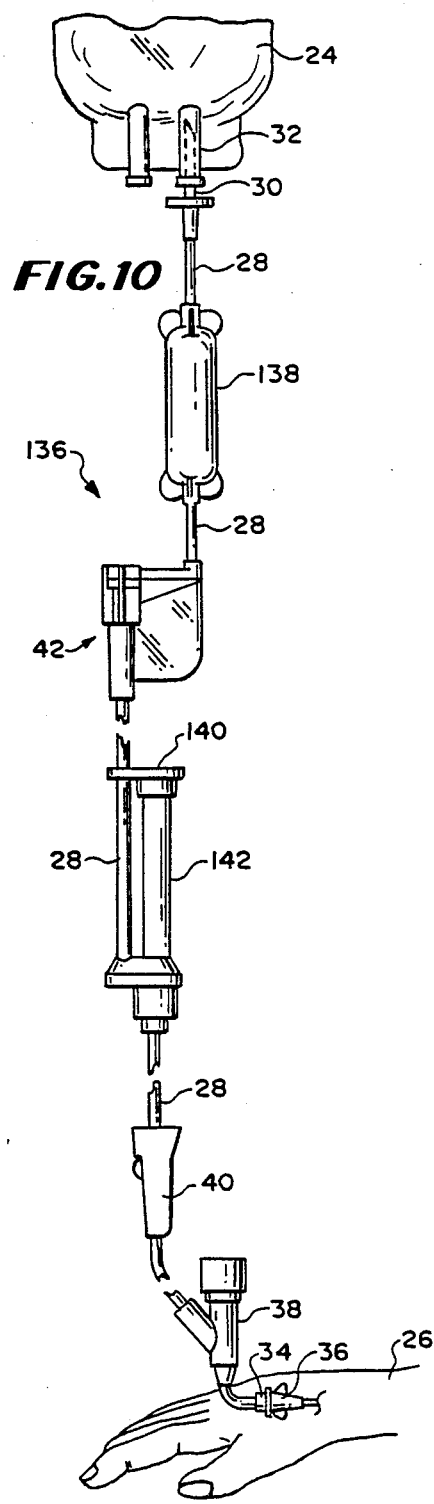
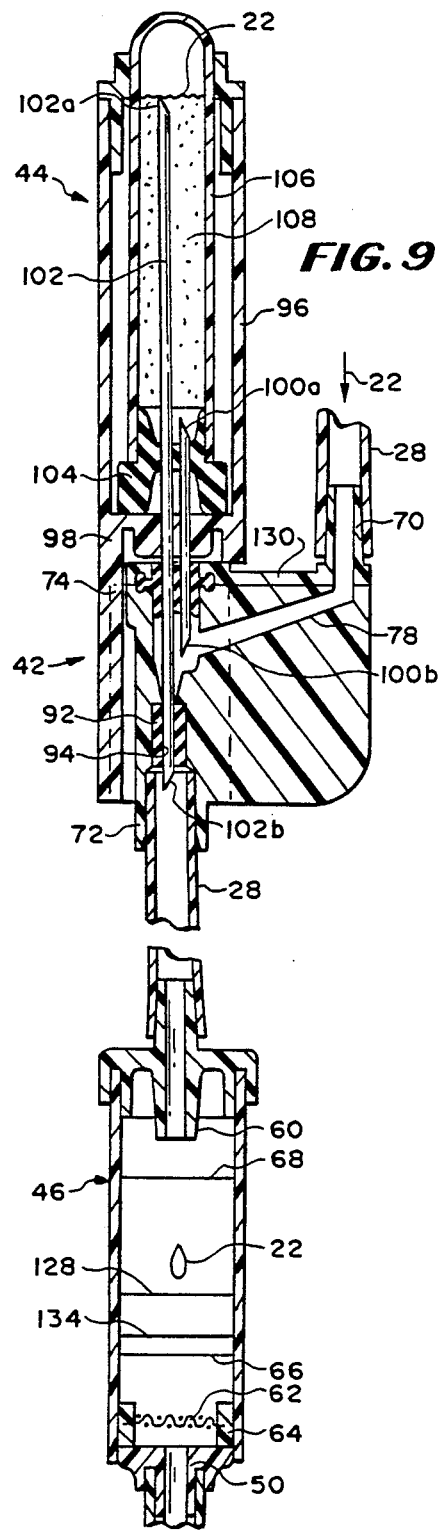

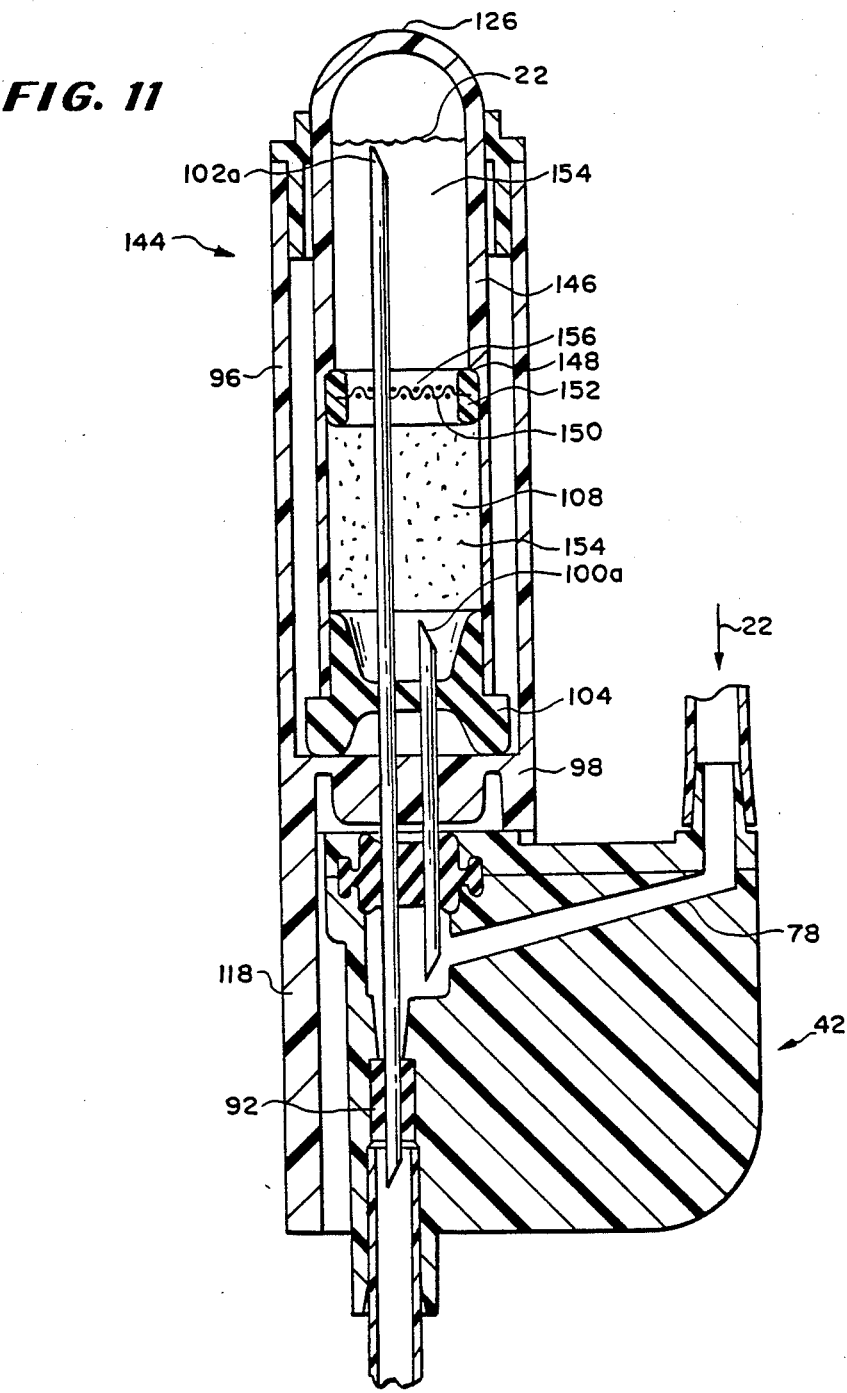

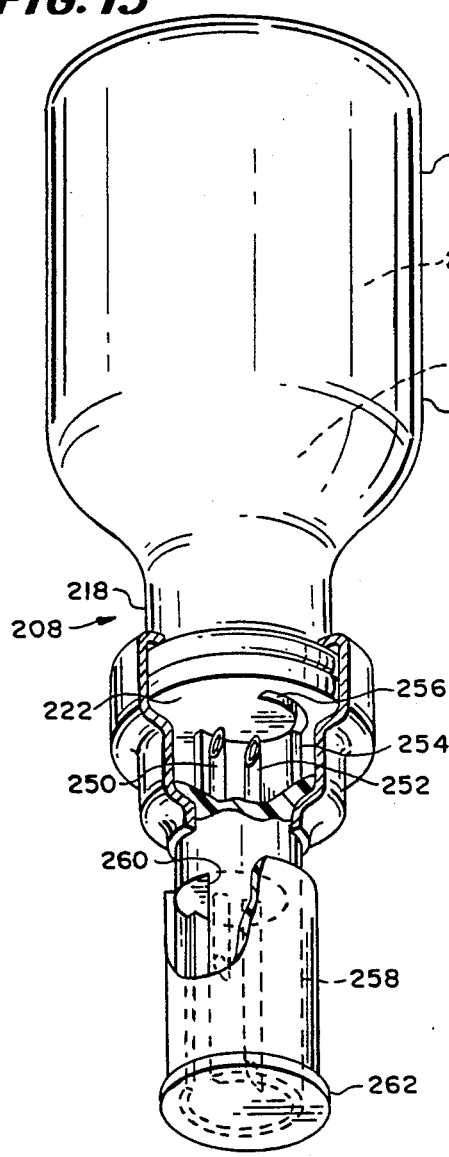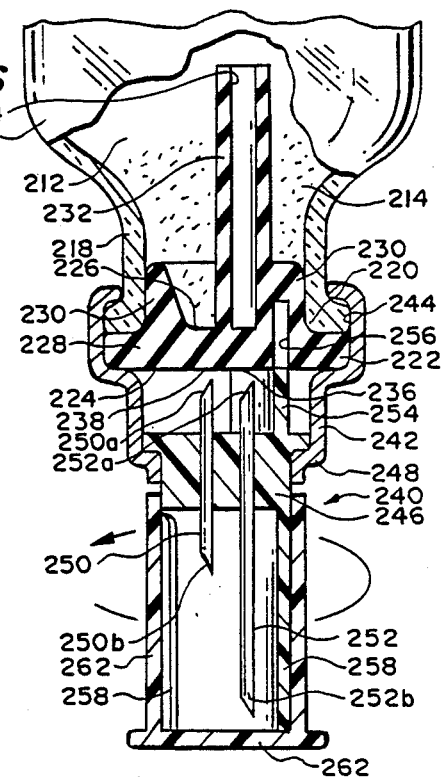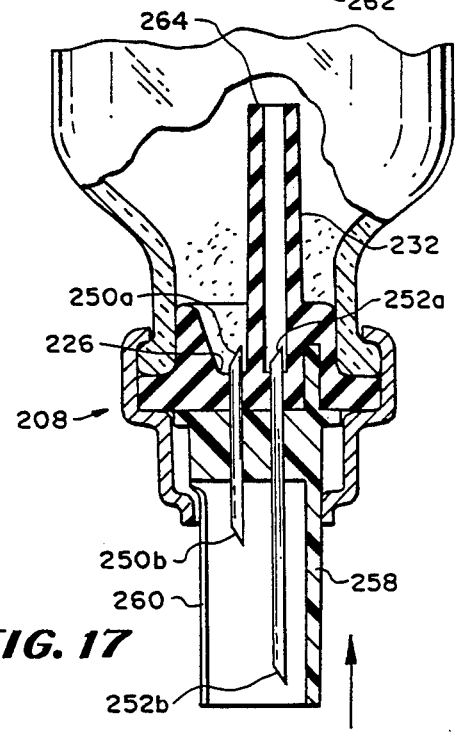

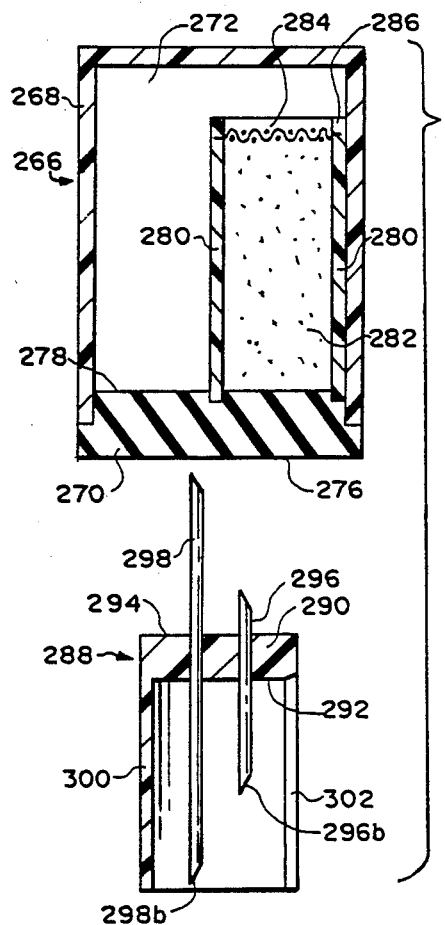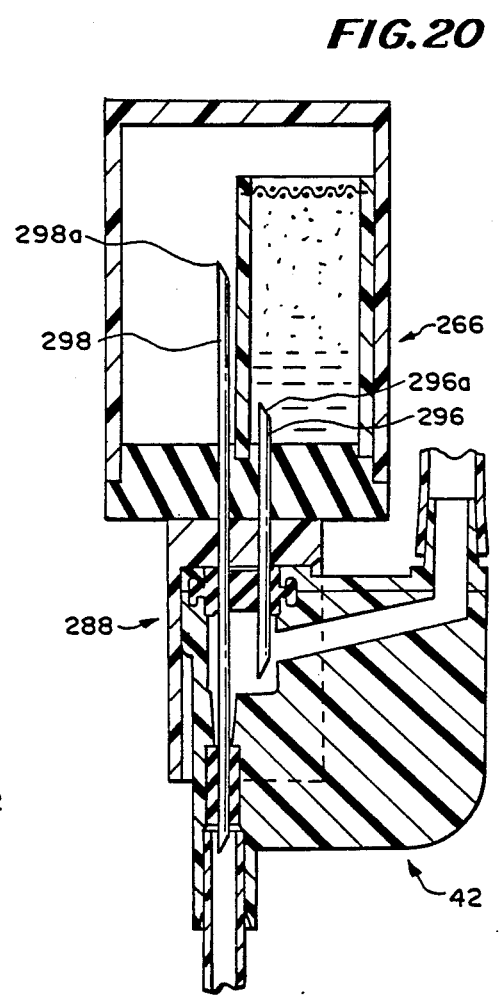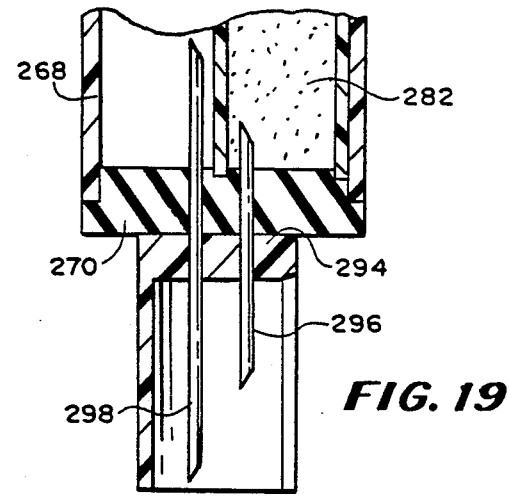

DRUG DELIVERY APPARATUS INCLUDING BENEFICIAL AGENT CHAMBER WITH CHIMNEY FOR A DIRECTED FLOW PATH

This application is a continuation of application Ser. No. 119,287, filed Nov. 5, 1987, now abandoned, which is a continuation of application Ser. No. 868,826, filed May 29, 1986, now abandoned.

The present application is filed concurrently with the following three applications that claim subject matter disclosed but not claimed in the present application: "Passive Drug Delivery System", Brian D. Zdeb et al., U.S. Ser. No. 07/262,209; "Drug Delivery Apparatus Creating Liquid Outflow Strata Having Different Drug Concentrations", Thomas J. Roeser et al., U.S. Ser. No. 07/119,262 (abandoned); and "Drug Delivery Apparatus Having a Piston-Like Injection Site", Stephen C. Jepson et al. U.S. Ser. No. 07/119,207 (abandoned).

TECHNICAL FIELD OF THE INVENTION

The present invention is related to the delivery of a beneficial agent to a patient and is more particularly directed to the passive delivery of the beneficial agent to the intravenous system of a patient in a safe and effective manner.

BACKGROUND OF THE INVENTION

Many drugs are mixed with a diluent before being delivered intravenously to a patient. The diluent may be, for example, a dextrose solution, a saline solution or even water. Many such drugs are supplied in powder form and packaged in glass vials or ampules. Other drugs, such as some used in chemotherapy, are packaged in glass vials or ampules in a liquid state.

Powdered drugs may be reconstituted in a well known manner, utilizing a syringe which is used to inject liquid into the vial for mixing, the syringe eventually withdrawing the mixed solution from the vial. When a drug must be diluted before delivery to a patient the drug is often injected into a container of diluent after it is reconstituted, where the container may be connected to an administration set for delivery to a patient. More specifically, the diluent is often packaged in glass bottles, or flexible plastic containers such as are sold under the names MINI-BAG TM AND VIA-FLEX ® by Travenol Laboratories, Inc. of Deerfield, Illinois. These containers have administration ports for connection to an administration set which delivers the container contents from the container to the patient. The drug is typically added to the container through an injection site on the container.

Drugs may be packaged separately from the diluent for various reasons. One of the most important reasons is that many drugs do not retain their chemical and physical stability when mixed with a diluent and thus cannot be stored for any substantial period of time. Also, drugs are often packaged separately from the diluent because many firms which manufacture drugs are not engaged in the business of providing medical fluids in containers for intravenous delivery, and vice versa.

Therefore, a doctor, nurse, pharmacist or other medical personnel must mix the drug and diluent. This presents a number of problems. The reconstitution procedure is time consuming and requires aseptic technique. The operator must provide the proper diluent and a syringe before beginning. Often the powdered drug is "caked" at the bottom of the vial. Thus, when liquid is injected into the vial from a syringe the surface area of contact between the liquid and the powdered drug may be quite small initially, thus making the mixing procedure even more time consuming. Because of the limited vial volume, the increasing drug concentration in the diluent makes it harder to finish the reconstitution process. The operator may attempt to solve this by repeatedly injecting solution into the vial, mixing and withdrawing the solution but this makes necessary additional injections and movement of the syringe which increase the likelihood of contamination. Also, it is sometimes difficult to get all of the drug and/or liquid out of the vial, thus increasing the time required to perform the reconstitution procedure.

The reconstitution procedure should be performed under preferably sterile conditions. In addition to such a requirement making the operator justifiably more cautious and consuming more time, sterile conditions are often hard to maintain. In some instances, a laminar flow hood may be required under which the reconstitution procedure is performed.

Some drugs, such as some chemotherapy drugs, are toxic. Exposure of the operator to the drugs during reconstitution may be dangerous, especially if the operator works with such drugs on a daily basis and is repeatedly exposed to them.

A further problem is that the reconstitution procedure provides a source of confusion as to which container contains which drug. The diluent container should be marked with the drug with which it has been injected and the name of the patient to whom it should be delivered.

After a drug is reconstituted and withdrawn into a syringe barrel, the drug may in some instances be injected immediately into the intravenous system of a patient. More typically however, the reconstituted drug is injected from the syringe into a larger container of solution as discussed above, for connection to an intravenous administration set. This is because often the drug reconstituted in the syringe is still at a concentration so high as to cause local toxicity in the veins of a patient near the injection site where the needle pierces the skin. This may create severe vein irritation which may be medically harmful. Additionally, even though the proper dose of medication is in the syringe, immediate injection into the patient's blood stream may create a condition of systemic toxicity wherein the level of drug concentration in the patient's entire blood stream is dangerously high. Yet another reason for not making the injection from the syringe directly into the patient is that it creates an additional injection site into the patient, which may be painful for the patient and provides another opportunity for infection.

For these reasons, the reconstituted drug is more typically injected into a diluent container.

A patient may typically be administered a dextrose or saline solution from a large volume parenteral container, for example, such as a one liter container, delivered through an administration set such as a CONTINU-FLO ® administration set sold by Travenol Laboratories. If the reconstituted drug were injected into the large volume parenteral container, delivery of the drug would usually be delivered over too long a time period. Often, these large volume fluids are delivered at very slow flow rates.

More typically, the reconstituted drug is injected into a small volume parenteral container, such as a fifty milliliter container sold by Travenol Laboratories. This MINIBAG TM container is hung at a higher elevation than the large volume parenteral container and is connected by a secondary administration set to an injection site on the primary administration set. Because it is maintained at a higher elevation, the reconstituted drug in the small volume container is delivered, after which fluid from the large volume container begins to flow once more. By utilizing a small volume container connected to an administration set for delivery of the drug or other beneficial agent instead of a direct syringe injection, the drug is delivered over a preferred time period that tends to minimize negative side effects.

A closed reconstitution delivery system is disclosed in U.S. Pat. Nos. 4,410,321; 4,411,662; 4,432,755; and 4,458,733, all assigned to Baxter Travenol Laboratories, Inc., the assignee of the present invention. As shown therein, a container includes a drug and a diluent in separate compartments which are reconstituted in a closed system before the drug is delivered to the patient. Typically, the container is connected to an administration set which is connected at its other end to the primary administration set, such as with the small volume parenteral container described above. The container shown in these patents solves many of the problems associated with syringe reconstitution. The product does however necessitate a series of reconstitution steps which must be performed by the nurse or other operator prior to delivering the fluid from the container.

Delivery of a drug or other beneficial agent in a manner not requiring reconstitution steps by an operator is shown in U.S. Pat. Nos. 4,424,056; 4,432,756; 4,439,183; 4,474,574; 4,479,793; 4,479,794; 4,525,162, and 4,548,599 and Canadian Pat. No. 1,173,795, assigned to Alza Corporation of Palo Alto, Cal. As disclosed in those patents, a parenteral delivery system is disclosed which has a formulation chamber therein for administering a beneficial agent such as a drug. The system is advantageous in that it provides for reconstitution of the drug by fluid flowing from a large volume parenteral container for example, through the administration set containing the formulation chamber with the drug therein. The system intends to eliminate the need for the time consuming reconstitution procedure described above and appears to eliminate the problems associated with the reconstitution procedure.

Another passive reconstitution system is disclosed in European patent application No. 0059694 to Aktiebolaget Hassle of Sweden.

Still another device for delivering a drug "in-line", i.e., in the administration set, is disclosed in U.S. Pat. No. 4,534,757 assigned to Alza Corporation. The device holds the drug and includes a section through which the liquid passes in a direction substantially opposite to the general direction in which liquid flows to the patient.

Yet another system which attempts to provide for drug reconstitution in-line without manual reconstitution by a nurse or other operator is shown in U.S. Pat. No. 4,465,471, assigned to Eli Lilly and Co. of Indianapolis, Ind. That patent discloses constructions for a receptacle in the administration set itself. A separate cartridge containing the drug to be reconstituted and delivered to the patient is plugged into the receptacle. As liquid enters the cartridge for reconstitution of the drug and subsequent delivery out of the cartridge and receptacle and into the patient, some or most fluid continues to flow through the administration set, bypassing the cartridge entirely.

European patent application Publication No. 0146310 to Eli Lilly and Co. is directed to a system for drug reconstitution including an intravenous administration set and a drug vial and utilizes the vial vacuum to reconstitute the drug.

U.S. Pat. No. 4,534,758 to Akers et al. discloses a relatively complex drug delivery apparatus with various valves. When liquid from a container is delivered to the drug vial, the vial is to be agitated for a time sufficient to suspend the previously dry medicine.

U.S. Pat. No. 4,581,014 to Millerd et al. assigned to Ivac Corporation of San Diego, Cal. discloses a selector valve for delivering a previously reconstituted drug from a drug vial through an intravenous administration set to a patient.

All the publications described above are directed to solutions to the time consuming reconstitution procedure and/or its associated problems, such as delivery of the solution to a patient. In most of the offered solutions, delivery of the drug is intended to be passive, i.e., once the drug is placed into the administration set, manual reconstitution steps are not required.

Still another common feature of many of the attempted solutions disclosed in these publications is that delivery of the drug is intended to be able to be made in a manner which is essentially independent of the fluid flow rate through the administration set and into the patient. Stated differently, some of the systems are designed to deliver a certain dosage of drug in a preselected time period, within a broad range of fluid flow rates. Delivery of a drug independent of flow rate is desirable because it ensures that the necessary dosage will be delivered within a therapeutically acceptable time period, which may be typically about twenty to thirty minutes, although this time period may vary depending upon the drug and dosage.

By making delivery of the drug or other beneficial agent independent of the flow rate, the system ensures that the drug will not be delivered too quickly should the flow rate be set too high by the nurse or other operator, thereby preventing the problem of systemic toxicity discussed above.

Some of the documents, such as U.S. Pat. Nos. 4,424,056; 4,479,793; and 4,479,794, and also directed to systems having a beneficial agent placed "in-line" in an administration set for mixing of the agent and delivery to a patient, wherein the delivery of the agent may be made in a given volume of fluid. Also, a valve controlling fluid flow may be manually operated to deliver the agent in a manner which can be made dependent upon fluid flow.

At least the automatic reconstitution type systems discussed above, (i.e., those not requiring a separate agitation or mixing step), suffer from the possibility of creating a concentration of beneficial agent in the fluid being delivered to the patient which is too high at low flow rates. This results in local toxicity to the patient near the point of introduction into the body. The problem is solved by the invention disclosed in U.S. patent application Ser. No. 721,999, filed Dec. 3, 1984, entitled "Drug Delivery Apparatus Preventing Local and Systemic Toxicity", Thomas E. Needham et al., assigned to the assignee of the present invention. Further solutions to the problems of passively mixing and delivering a beneficial agent to a patient are disclosed in U.S. patent application Ser. No. 721,991 filed Dec. 3, 1984 entitled "Housing Enabling Passive Mixing of a Beneficial Agent with a Diluent", Brian Zdeb et al., also assigned to the assignee of the present invention. In that application there is disclosed certain housing constructions for delivering the beneficial agent to the patient. Typically, the housing includes a receptacle which is placed in-line in a medical liquid administration set and a separate cartridge including the beneficial agent. The cartridge is plugged into the receptacle when it is desired to deliver the beneficial agent to the patient. Active reconstitution by a nurse or other operator is not required. Instead, once the cartridge is plugged into the receptacle, liquid flowing from the source of medical liquid through the administration set flows into the receptacle and the agent-containing cartridge, reconstituting the agent. The solution with agent therein flows out the receptacle, down the administration set to the patient's venous system.

It would be desirable to have an administration set adapted for the passive mixing and delivery of a beneficial agent to a patient, which does not require any communication with the external environment.

It would be desirable to have in the administration set a receptacle of a construction which may be easily manufactured and which simply and effectively permits securement of the cartridge thereto. It would be desirable to provide a receptacle which assures that liquid flowing into the receptacle flows through the cartridge without any leakage that would bypass the cartridge.

It would further be desirable to have a receptacle including an improved pierceable situs which can withstand repeated insertions and removals of one or more cannulas during repeated use of a plurality of cartridges in the single receptacle, without the possibility of the inadvertent removal of the pierceable situs.

It would be desirable to have a cartridge containing a beneficial agent, of a design which is low in cost and easy to manufacture, providing for simple, quick and properly aligned mounting on the receptacle.

It would also be desirable, for a given cartridge design, to vary the preselected drug concentration of fluid exiting the cartridge downstream to the patient.

It would be desirable to provide a cartridge containing a beneficial agent wherein the cartridge design assures a proper fluid flow path for delivery of the proper amount and concentration of drug to the patient.

SUMMARY OF THE INVENTION

The present invention provides improvements in a cartridge containing beneficial agent that is delivered by combination with a medical liquid to a patient. The cartridge is designed for mounting upon a receptacle in an intravenous administration set for introducing the beneficial agent into the fluid conduit of the administration set, enabling passive reconstitution of the drug or other agent during fluid flow through the cartridge. The cartridge includes a wall defining a chamber with the beneficial agent therein and pierceable closure means closing the chamber.

The closure means, which in a preferred embodiment includes a pierceable stopper, includes a hollow, open ended protrusion extending from the inner face of the stopper in a direction substantially parallel to the length of the cartridge. The beneficial agent is retained within the hollow, open ended protrusion by means of a liquid pervious barrier such as a particulate matter barrier. The particulate matter barrier in the preferred embodiment includes a screen having nominal pour size of no greater than about 20 microns and most preferably about 5 to 10 microns.

The cartridge further includes a flow connector adapted for mounting to the defined chamber and including in one embodiment cartridge connection means, a base mounted to the connection means, and two hollow cannulas mounted within the base in a direction substantially parallel to the hollow, open ended protrusion within the cartridge chamber. The base and hollow cannulas are slidable relative to the pierceable stopper. In a first position, the hollow cannulas are spaced from the chamber. In a second position, the first and second cannulas have both pierced the stopper into the chamber. In this second position, the first cannula has piercing the stopper in alignment with the hollow, open ended protrusion, while the second cannula has pierced the stopper at a point external to the hollow, open ended protrusion, thereby creating the desired flow path through the chamber for desired mixing or delivery of the beneficial agent to a patient.

Liquid flowing through the administration set enters the receptacle upon which the cartridge is mounted. All liquid entering the receptacle enters the first cannula and flows into the hollow, open ended protrusion. The liquid level in the hollow, open ended protrusion rises as it rises with the beneficial agent until it reaches the top of the hollow, open ended protrusion, whereupon liquid flows down the side of the hollow, open ended protrusion, and out the receptacle through the second cannula to the remainder of the administration set to the patient.

In the preferred embodiment of the invention, the base with the cannulas is rotatable relative to the pierceable closure means and the drug chamber. The pierceable closure means and the base include a mating key and keyway which, when aligned, cause the first cannula to be in alignment with the hollow, open ended protrusion for piercing the closure means.

DESCRIPTION OF THE DRAWINGS

FIG. 1 is a perspective view of an administration set including the air flask and the receptacle;

FIG. 2 is an enlarged, fragmentary, cross-sectional view of the receptacle illustrated in FIG. 1;

FIG. 3 is a fragmentary, enlarged, cross-sectional view of the air flask illustrated in FIG. 1;

FIG. 4 is a side elevational view of a cartridge for beneficial agent to be used with the administration set of FIG. 1, illustrating the cartridge chamber in the first position;

FIG. 5 is a side elevational view as in FIG. 4, with the cartridge chamber having been slidably moved to its second position;

FIG. 6 is a fragmentary cross-sectional view of the closure for the cartridge chamber;

FIG. 7 is a fragmentary perspective view of the administration set prior to mounting the cartridge upon the receptacle;

FIG. 8 is a view similar to FIG. 7, illustrating the cartridge mounted upon the receptacle;

FIG. 9 is a fragmentary, cross-sectional view of the administration set, illustrating the receptacle, the cartridge and the air flask in fluid communication;

FIG. 10 is a side elevational view of another embodiment of the administration set;

FIG. 11 is a cross-sectional view of still another embodiment of the cartridge;

FIG. 15 is a cutaway, perspective view of a cartridge including a chimney within the cartridge chamber for establishing a directed flow path therein;

FIG. 16 is a longitudinal, cross-sectional view of the cartridge of FIG. 15;

FIG. 17 is a cross-sectional view of the cartridge of FIG. 15, after flow communication between the chamber and the adapter has been established;

FIG. 18 is an exploded, longitudinal cross-sectional view of another embodiment of a cartridge including a chimney therein;

FIG. 19 is a cross-sectional view of the cartridge of FIG. 18, after flow communication between the cartridge chamber and the adapter has been established;

FIG. 20 is a cross-sectional view of the cartridge of FIG. 18, secured to the receptacle;

DETAILED DESCRIPTION

Figure 9A:
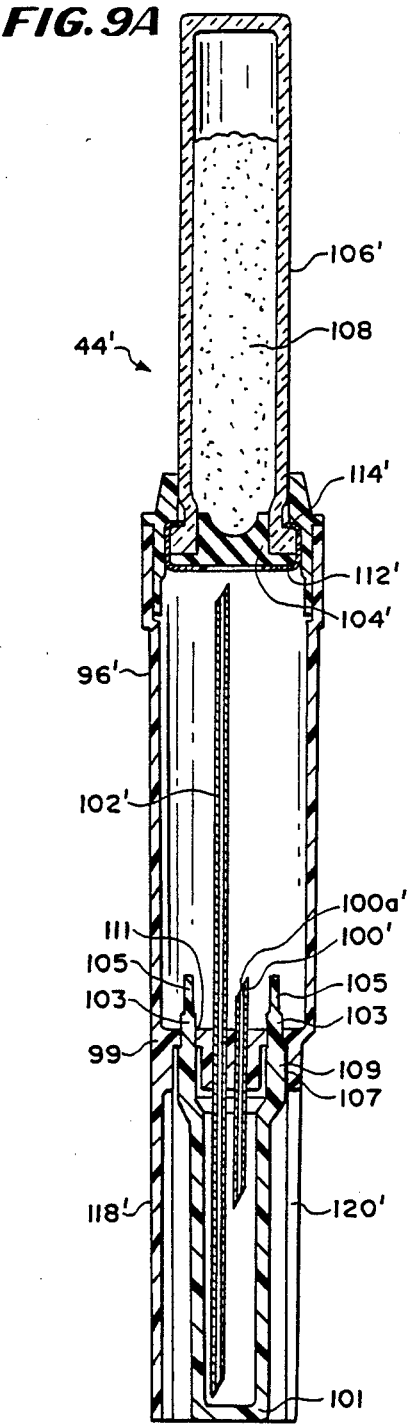
FIG. 9A is a cross-sectional view of another embodiment of the cartridge, with the cartridge chamber in the first position.

Referring to FIG. 1, there is illustrated an administration set 20 for the delivery of a medical liquid, stored within a medical liquid source such as large volume parenteral container 24, to a patient 26. The administration set 20 includes a fluid conduit 28 made for example of flexible polyvinylchloride tubing. Upstream connection means such as a standard intravenous administration set spike 30 is mounted at the upstream end of the fluid conduit 28. The spike is adapted for piercing the membrane of the container administration port 32.

The fluid conduit 28 includes downstream connection means such as a Luer taper 34 mounted at the downstream end of the fluid conduit 28. The Luer taper 34 may be connected in accordance with standard technique to a venous catheter 36.

The administration set 20 may further include a standard pierceable injection site 38 for injecting a medical liquid by means of a needle through the injection site 38. The administration set 20 may further include flow rate control means such as a standard roller clamp 40 mounted about the flow conduit 28.

The administration set 20 further includes a unique receptacle 42 shown in greater detail in FIG. 2. The receptacle 42 is an improvement to the receptacle disclosed in co-pending U.S. patent application Ser. No. 721,991, filed Dec. 3, 1984. The receptacle 42 is mounted along the fluid conduit and is adapted for receiving a separate cartridge 44 containing beneficial agent, illustrated in FIGS. 4 through 9 and 10. When the cartridge is mounted upon the receptacle, at least some, and preferably all liquid from the medical liquid source container 24 that flows through the fluid conduit 28 into the receptacle 42 also flows through the cartridge 44 before passing downstream out of the receptacle to the patient.

Downstream of the receptacle 42 is an air flask or chamber 46, illustrated in FIGS. 1, 3, 7, 8 and 9. As will be explained in greater detail below, the air flask 46 permits automatic priming of the cartridge 44 upon mounting of the cartridge on the receptacle 42 of the administration set 20. The air flask 46 absorbs the air disposed within the cartridge 44 and prevents that air from passing downstream to the patient.

Referring to FIG. 3, the air flask 46 includes an inlet 48 mounted to and receiving fluid from upstream fluid conduit 28a. The air flask 46 includes an outlet 50 mounted to and transferring liquid to downstream fluid conduit 28b. The inlet and outlet may be mounted to the fluid conduit 28 by means of interference fit, solvent bonding etc. The air flask 46 is mounted downstream of the receptacle 42.

In the preferred embodiment the air flask 46 includes inlet and outlet end caps 52, 54 respectively between which is mounted a cylindrical sidewall 56 of preferably optically transparent, flexible material such as polyvinyl chloride. The sidewall 56 and the end caps 52, 54 define an air chamber 58 having a cross-sectional diameter that is greater than the internal diameter of the fluid conduit 28, so that liquid entering the air chamber 58 from the drop forming orifice 60 adjacent the inlet 48 falls toward the outlet 50. The air flask 46 thus provides a collection reservoir for air within the administration set 20.

The air flask 46 further includes particulate matter barrier means such as a particulate matter screen 62 mounted within a plastic ring 64 near the outlet 50. The particulate matter barrier may in fact be a sterilizing filter having nominal pore size of about 0.2 micron. The nominal pore size may be much larger, such as a gross particulate matter barrier having a nominal pore size of about 20 microns. In the preferred embodiment the nominal pore size is about 10 microns. The screen may be a nylon mesh material such as supplied by Filter Tek of Hebron, Ill. The particulate matter barrier 62 is mounted transverse to the fluid path such that all liquid passing through the air flask 46 must pass through the particulate matter barrier 62.

The particulate matter barrier 62 need not be disposed within the air flask 46 but the barrier should be mounted downstream of the receptacle 42 so that all liquid that exits the inserted cartridge 44 will pass through the particulate matter barrier. Also, it is possible to construct the receptacle 42, the air flask 46 and the particulate matter barrier 62 as a single unit rather than as separated by upstream fluid conduit 28a for example.

In the preferred embodiment, the air flask 46 includes a minimum liquid level indicator 66 and a maximum liquid level indicator 68 which may for example comprise lines around the periphery of the air flask 46. The liquid level in the air flask 46 should preferably be somewhere between the minimum and maximum liquid level indicators 66, 68 immediately before insertion of the cartridge 44 within the receptacle 42.

The improved receptacle 42 includes a receptacle inlet 70 and a receptacle outlet 72 connected to the fluid conduit 28. The air flask 46 is disposed downstream of the receptacle outlet 72.

The receptacle 42 includes upper and lower fitments 74, 76 respectively. The upper fitment 74 includes the inlet. The lower fitment 76 includes the outlet 72 and a fluid receiving segment 78 having an upstream end in fluid communication with the inlet 70 and a downstream end in fluid communication with the outlet 72.

Pierceable situs 80 is mounted within the receptacle 42, trapped between the upper and lower fitments 74, 76. The pierceable situs 80 includes a pierceable main body portion 82 and a ring-like extension 84 extending about the periphery of the main body portion 82. The ring-like extension 84 further includes an enlarged outer periphery 86.

Together, the upper and lower fitments 74, 76 define an annular channel 88 substantially corresponding to and receiving the ring-like extension 84 including the enlarged periphery 86 thereof, such that the upper and lower fitments trap the pierceable situs 80 therebetween in secure fashion. The situs 80 may not be removed without destruction of the receptacle 42. The upper and lower fitments 74, 76 may be bonded together by adhesive, ultrasonic sealing etc. It is important that the situs be securely maintained within the receptacle because a plurality of cartridges 44, each having two piercing cannulas, may be repeatedly inserted and withdrawn from the situs during the useful life of the receptacle 42 and administration set 20. The fluid receiving segment 78 includes a tapered portion 90 below and generally coaxial with the pierceable situs 80. The tapered portion 90 serves as a needle guide into the resilient bushing 92.

The resilient bushing is preferably made of an elastomer such as polyisoprene. The resilient busing 92 defines a narrow through-bore 94. The resilient bushing is juxtaposed relative to the pierceable situs 80 so that the through-bore 94 is substantially coaxial with the tapered portion 90.

Turning now to FIGS. 4 through 9 and 10 there is shown the cartridge 44 for introducing a drug or other beneficial agent into the fluid conduit 28 at the receptacle 42, for delivery of the agent to a patient.

The cartridge 44 includes a rigid cylinder 96 and a base plate 98 mounted across the rigid cylinder 96. First and second hollow cannulas 100, 102 respectively are mounted through the base plate 98 and extend within the rigid cylinder 96 on at least one side of the base plate in a direction substantially parallel to and inside the rigid cylinder 96. Each of the hollow cannulas 100, 102 extend on both sides of the base plate. The first hollow cannula 100 includes a pointed first end 100a adapted for piercing a pierceable stopper 104. The first hollow cannula 100 also includes a pointed second end 100b opposite the pointed first end 100a. Similarly, the second hollow cannula 102 includes a pointed first end 102a adapted for piercing the pierceable stopper 104. The second hollow cannula 102 also includes a second pointed end 102b opposite the pointed end 102a. The second hollow cannula 102 extends further from the base plate on both sides thereof than the first hollow cannula 100.

The cartridge 44 further includes a tubular chamber 106 containing a beneficial agent 108 such as a dry powdered drug, although the agent may also be a liquid. The pierceable stopper 104 or other closure means previously referred to above closes the tubular chamber 106.

Referring to FIG. 6, the pierceable stopper 104 is mounted within the mouth 110 of the tubular chamber 106. The rubber stopper 104 may be secured within the tubular chamber 106 by means of a metal band 112 about the periphery of the mouth 110 and the rubber stopper 104, in a manner similar to the securement of a stopper in a standard drug vial. The tubular chamber 106 is slidably mounted within the rigid cylinder 96 such that the rubber stopper 104 faces the base plate 98. The tubular chamber 106 is kept from total disengagement from the cylinder 96 by means of a lip 114 extending from the rigid cylinder 96. The lip 114 engages the stopper 104 and metal band 112 assembly that extends outwardly from the sidewall of the tubular chamber 106, as illustrated in FIG. 6. The pierceable stopper 104 may include a cone defining volume 116 facing the interior of the chamber 106. In place of the pierceable stopper, other pierceable closure means may be provided.

When the cartridge 44 is in a first position illustrated in FIGS. 4, 6 and 7 for example, the rubber stopper 104 has not been pierced through by either the first or second hollow cannulas 100, 102. In the preferred embodiment, the pierceable stopper 104 remains spaced from the first and second cannula 100, 102 when the tubular cartridge 106 is in the first position.

The first and second hollow cannulas 100, 102 comprise flow path means. The shorter, first hollow cannula 100 provides an inlet path into the tubular chamber 106. The longer, second cannula 102 provides an outlet path out of the chamber. The flow path means forms part of the adapter means, including the rigid cylinder, mounted about the chamber and adapted for mounting the cartridge 44 upon the receptacle 42. The adapter slides relative to the chamber 106. As will be seen later in other embodiments, the hollow cannulas 100, 102 may be slidable within the rigid cylinder. Stated differently, the tubular chamber and the adapter flow path means are selectively slidable relative to each other.

The adapter means may further include keyway means extending on the side of the base plate opposite of the chamber 106 and substantially coaxial therewith. The keyway means may include a relatively rigid keyway wall 118 including a keyway slot 120 for fitting over the receptacle 42. The keyway wall 118 may also include one or more longitudinal defined channels 122 for engaging corresponding longitudinal keys 124 mounted about the exterior of the receptacle 42. The keyway means ensures proper engagement of the cartridge 44 with the associated receptacle 42, including the proper disposition of the first and second hollow cannulas 100, 102 within the receptacle 42.

The chamber 106 of the cartridge 44 is slidable from the first position shown in FIG. 4 for example to a second position illustrated in FIG. 5 obtained by pushing the chamber 106 down within the rigid cylinder 96 until the pierceable stopper 104 abuts the base plate 98, which serves as a stop. In this position, both the first and second cannulas 100, 102 have pierced the pierceable stopper 104, so that the pointed hollow ends 100a, 102a of the first and second cannulas 100, 102 are in communication with the chamber interior. The end 102a of the second hollow cannula is well within the tubular chamber, preferably near the top end 126 of the chamber 106. The pointed hollow end 100a of the first cannula 100 is preferably just within the tubular chamber 106, such as within the hollow conical portion 116 defined by the stopper 104.

In operation, before a beneficial agent 108 in the cartridge is delivered to the patient, the administration set 20 of the invention operates by providing an open fluid pathway between the medical liquid container 24 and the patient 26, as illustrated in FIG. 1. Liquid 22 flows from the container 24 through the administration port 32 and spike 30. The liquid flows through the fluid conduit 27 and through the receptacle 42, following the pathway through the receptacle inlet 70, fluid receiving segment 78, tapered portion 90, through-bore 94 and outlet 72, in that order. Liquid flows through the connecting conduit 28 and into the air flask 46 through the drop former 60. Air collects within the air flask 46 and liquid continues to flow downstream through the flask outlet 50 through the downstream conduit portion 28b and into the patient through the Luer connection 34 and venous catheter 36.

Before the administration set 20 is placed in communication with the patient 26, the fluid conduit 28 is primed, i.e., air is eliminated. This is performed in the known manner, by allowing liquid to flow through the set 20 before connection to the patient.

To raise the liquid level up to a level 128 within the flask 46 such that it is between the minimum and maximum indicator lines 66, 68, the air flask sidewall 56 may be squeezed and released such as with most drip chambers, in the standard manner.

When it is desired to deliver a beneficial agent 108 such as a drug to the patient, the cartridge 44 having the beneficial agent 108 therein is mounted upon the receptacle 42. FIG. 7 illustrates the cartridge 44 and receptacle 42 before activation of the cartridge and before it is mounted on the receptacle.

The cartridge is provided to the nurse or the medical personnel as illustrated in FIGS. 4 and 7, with the chamber 106 in the first position. The cartridge is activated simply by grasping the rigid cylinder 96 and pushing down on the top 126 of the chamber 106 with the thumb. This forces first the second cannula end 102a and then the first cannula end 100a through the pierceable stopper 104. The tubular chamber 106 is urged downwardly until further movement is limited by contact between the pierceable closure 104 and the base plate 98. This second position is illustrated in FIG. 5.

With the cartridge 44 now in the second position, the cartridge is then mounted upon the receptacle 42 as illustrated in FIG. 8. It is important that the first and second cannulas 100, 102 be disposed in a particular position within the receptacle 42. This is provided for by the keyway wall 118 having the keyway slot 120 therewithin, the slot 120 being guided over the bridge 130 of the upper fitment 74 on the receptacle 42; and is further provided for by the longitudinal defined channels 122 within the keyway wall 118, which fit over the plurality of longitudinal keys 124 mounted about the receptacle 42. In the preferred, illustrated embodiment the keyway wall 118 includes three defined channels 122 for mating with three longitudinal keys 124 on the receptacle.

Referring to FIG. 9, the cartridge 44 is easily mounted upon the receptacle 42 in the manner shown in FIG. 8 by grasping the receptacle 42 at the handle 132 in one hand and the rigid cylinder 96 in the other hand and pushing the cartridge down so that the second end 102b of the second cannula and then the second end 100b of the shorter, first cannula both pierce the main body portion 82 of the pierceable situs 80. The cartridge 44 continues to be urged downwardly so that the second hollow cannula 102 enters the through-bore 94 and is liquid-sealingly engaged by the bushing 92 around the periphery of the second hollow cannula 102. Proper installation has occurred after the base plate 98 abuts the top fitment 74, limiting further downward movement of the cartridge 44.

Upon engagement of the cartridge 44 and receptacle 42 as illustrated in FIG. 9, liquid 22 flowing into the receptacle at inlet 70 flows through the fluid receiving segment 78. The resilient bushing 92 has sealed about the second hollow cannula 102, preventing liquid 22 from passing immediately downstream. Instead, the liquid 22 enters the second end 100b of the first cannula 100 and enters the tubular chamber 106 at the first end 100a of the cannula.

As liquid 22 rises within the chamber 106, residual air within the chamber is forced downstream through the second hollow cannula 102. The air enters the air flask 46 through the drop former 60 and collects within the flask 46. The initial liquid level 128 illustrated in FIG. 1 drops to a new level such as indicated by line 134. The liquid level 128 should be above the minimum liquid level indicator line before insertion of the cartridge 44 into the administration set 20 so that as air exits the cartridge 44, the liquid level within the air flask 46 will not drop to the flask outlet 50 where it could be trapped and forced downstream to the patient. The liquid level 134 after cartridge priming may be below the minimum liquid level 66, but if it is above the minimum line 66 before insertion of the cartridge 44, the liquid level 134 will never be as low as the outlet 50.

The maximum liquid level indicator 68 serves as a guide for the maximum liquid level so that liquid drops entering the air flask through the drop former 60 may still be counted in the manner of a standard drip chamber.

The liquid level within the tubular chamber 106 continues to rise until it reaches the hollow pointed end 102a of the second cannula 102, whereupon liquid 22 begins to exit the chamber 106 through the second cannula 102, downstream through the second end 102b and into the air flask 46 through the drop former 60. Liquid exiting the chamber 106 has an appropriate concentration of beneficial agent 108 mixed therewith for delivery to the patient. The upward liquid flow path created within the chamber 106 by the first and second cannulas 100, 102 creates a density gradient within the chamber 106 such that the concentration of drug within the liquid 22 exiting at cannula end 102a will not be so high as to create local toxicity to the patient. Local toxicity is a situation in which vein irritation can occur near the venous injection site when drug concentrations within the delivery liquid 22 are too high.

At typical liquid flow rates, the amount of drug delivered to the patient per unit time is generally independent of the flow rate. This means that at extremely high flow rates, the total amount of drug delivered to the patient per unit time will not be so high as to cause systemic toxicity to the patient. Stated differently, the patient will not have too much drug introduced into the body in too short a time period.

It is believed that at lower liquid flow rates the rate of drug delivered to the patient per unit time tends to become more dependent upon the liquid flow rate through the administration set 20. However, local toxicity to the patient will not occur. It is believed that the upper limit on the drug concentration within liquid 22 exiting the chamber 106 is limited to a safe maximum for two principle reasons. First, the density gradient created within the columnar tubular chamber 106 means that the concentration of liquid 22 at the point of entry into the second cannula 102 is the lowest of any elevation within the tubular chamber 106. Secondly, as the liquid flow rate through the administration set 20 decreases, which would ordinarily increase the risk of an unacceptably high drug concentration to the patient, the amount of mixing and liquid turbulence created within the chamber 106 also decreases, exaggerating the density gradient so that the difference in densities from the area of the stopper 104 to the first end 102a of the second cannula 102 becomes greater.

It is to be noted that the different liquid flow rates mentioned above are only possibilities; in the preferred manner of operation, the nurse or other medical personnel would set an acceptable flow rate with the flow rate control means (such as the roller clamp 40 or a peristaltic pump) and not adjust the liquid flow rate again, at least until after delivery of the beneficial agent 108.

The administration set 20, with the unique cartridge 44 and receptacle 42, are capable of delivering a therapeutically beneficial amount of a beneficial agent 108 within a therapeutically acceptable time period. For example, a one gram dose of ampicillin in the chamber 106 may be delivered in about thirty minutes at a liquid flow rate of 120 mls per hour.

In the preferred embodiment, the tubular chamber 106 has a volume of about 10 mls, and may include up to about 3 to 4 mls of air. The internal diameter of the tubular chamber is about 0.4 inch. The height of the tubular chamber from the mouth 110 to the top 126 is about two inches. As described in U.S. patent application Ser. No. 721, 991 filed Dec. 3, 1984, the hollow conical portion 116 of the pierceable stopper closure 104 is believed to assist in mixing, creating additional turbulence at the point of entry of liquid 22 at the first end 100a of the first cannula 100. The relatively long, narrow configuration of the chamber 106 is also believed to assist in mixing the beneficial agent 108 with the liquid 22. The liquid 22 may be a 5% dextrose solution for example.

It is to be noted that by varying the dimensions of the tubular chamber 106 the delivery profile for the beneficial agent 108 may be changed. For example, by enlarging the internal diameter of the tubular chamber, it will take longer to deliver the agent 108 within the chamber 106 to the patient 26. Similarly, lengthening the chamber 106 will also increase the delivery time if the second cannula 102 is also extended within the longer chamber 106.

Another administration set 136 for delivering a beneficial agent 108 utilizing the receptacle 42 and cartridge 44 of the invention is illustrated in FIG. 10, wherein like elements are referred to by the same numbers. The administration set 136 includes a standard flexible plastic drip chamber 138 for counting drops and to assist in priming the set 136. The receptacle 42 is mounted in the set, such as downstream of the drip chamber 138.

An air flask 46 is not included. Other means is provided to vent the air from one or more cartridges 44 as they are installed upon the receptacle 42. For this purpose, an air vent 140 is provided downstream of the receptacle 42. The air vent may comprise a bacteria-blocking, hydrophobic membrane. The air vent 140 may be part of a liquid filter, such as 0.22 micron sterilizing filter 142. Such a filter is disclosed in U.S. Pat. No. 4,568,366 to Frederick et al., assigned to the assignee of the present invention. That filter 142 includes hydrophilic-acting hollow fiber filter elements which remove any particulate matter from the liquid 22.

Figure 9B:
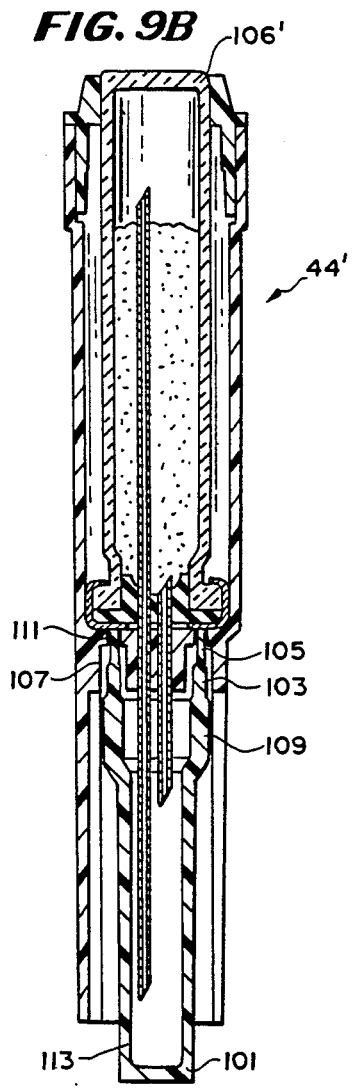
FIG. 9B is a cross-sectional view of the cartridge of FIG. 9A, with the cartridge chamber in the second position.

Referring now to FIGS. 9A and 9B, there is illustrated a cartridge 44' including a chamber 106', a rigid cylinder 96' and keyway wall 118' similar to the chamber 106, rigid cylinder 96 and keyway wall 118. A stopper 104' including a metal band 112' thereabout is mounted within and closes the chamber 106' which retains the beneficial agent 108. The lip 114' retains the tubular chamber 106' in functional engagement with the rigid cylinder 96'.

A base plate 99 extending across the rigid cylinder 96' includes first and second cannulas 100', 102' respectively.

The cartridge 44' of this embodiment also includes a cartridge-removable needle cover 101 removably secured within the base plate 99. The cartridge-removable needle cover 101 has as its principal purpose preventing the connection of the cartridge 44' to a receptacle 42 without first piercing the stopper 104' with the cannulas 100', 102'. Stated differently, the needle cover 101 ensures that the cartridge chamber 106' must be moved from the first position illustrated in FIG. 9A to the second position illustrated in FIG. 9B before the cartridge 44' can be mounted upon the receptacle 42. Should the cartridge be mounted prematurely, i.e., before the cartridge is moved to the second position, liquid flowing through the administration set would spill out of the first end 100a of the first cannula 100' without entering the cartridge chamber 106'.

Because of the relatively small dimensions of the keyway wall 118', the needle cover 101 cannot be removed from the cartridge 44' when the needle cover 101 is disposed as shown in FIG. 9A.

The needle cover 101 includes pins 103, including a reduced pin portion 105 at the distal end of each pin. The pins extend from a circular needle cover base 109. The base plate 99 includes an annular ring-like channel 107 which receives the needle cover base 109 therein. Openings 111 extend through the base plate 99 at points along the ring-like channel 107 and receive the pins 103, preferably in interference fit so that the needle cover 101 will not inadvertently become detached from the base plate 99.

When the tubular chamber 106' is moved to the second position illustrated in FIG. 9B in accordance with the description relative to the cartridge 44 and chamber 106 above, the pierceable stopper 104' or other closure means engages the pins 103 before abutting the base plate 99. This downward movement against the pins 103 forces the needle cover 101 out of the interference fit shown in FIG. 9A. The tip 113 of the needle cover 101 now projects beyond the end of the keyway wall 118' and so may be grasped and manually removed; alternatively, since the narrower pin portions 105 are now within the openings 111, there is no longer an interference fit between the base plate 99 and the needle cover 101, so that the needle cover 101 will now preferably simply fall out of the cartridge 44'.

After removal of the needle cover 101 the cartridge 44' is then secured to the receptacle 42 in the manner described above relative to the cartridge 44.

In addition to preventing improper mounting of the cartridge 44' upon the receptacle 42, the needle cover 101 also prevents touch contamination of the cannulas 100', 102'.

Referring now to FIG. 11, there is illustrated an alternate embodiment for a cartridge 144. Like elements retain the same reference numerals. In this embodiment the cartridge 144 still includes a rigid cylinder 96 and keyway wall 118. The tubular chamber 146 is closed by means of a pierceable closure such as stopper 104. The chamber 146 includes a step 148 for mounting a particulate matter barrier. The particulate matter barrier may include a five micron nylon mesh screen 150 for example mounted within a plastic ring 152 which is secured by means of heat seal or the like at the step 148. Before the cartridge 144 is used, the beneficial agent 108 continues to be trapped between the stopper 104 and the screen 150. No beneficial agent 108 is within the top end portion 154 of the chamber 146 on the far side 156 of the screen 150. The description as to the nominal pore size and materials concerning the particulate matter barrier 62 within the air flask 46 of FIG. 3 may apply as well to the particulate matter barrier 150.

Like the cartridge 44, the cartridge 144 is slidably received within the rigid cylinder 96. The cartridge is illustrated in FIG. 11 with the chamber 146 in the second position, with the first and second cannulas 100, 102 already piercing the stopper 104 and with the cartridge 144 already installed on the receptacle 42 for delivery of the beneficial agent 108 within a delivery liquid 22.

During operation, as the chamber 146 is slid into the second position, the second hollow cannula 102 pierces the particulate matter barrier 150 and extends into the upper portion 154 of the chamber 146 where no beneficial agent is stored. As liquid enters the chamber 146 through the first cannula 100, the beneficial agent 108 mixes with the liquid as in the earlier described embodiments. However, due to the particulate matter barrier 150, any beneficial agent entering the upper portion 146 has already been dissolved within the delivery liquid 22. Liquid 22 with beneficial agent 108 mixed therein flows up to the level of the second hollow cannula first end 102a, whereupon it is delivered downstream to the patient.

It is believed that by trapping the beneficial agent 108 in a lower portion 154 of the tubular chamber 146 that better mixing action may actually occur. As with the cartridges 44, 44', the cartridge 144 operates best when the first hollow cannula first end 100a is just barely within the chamber 146.

Figure 12A:
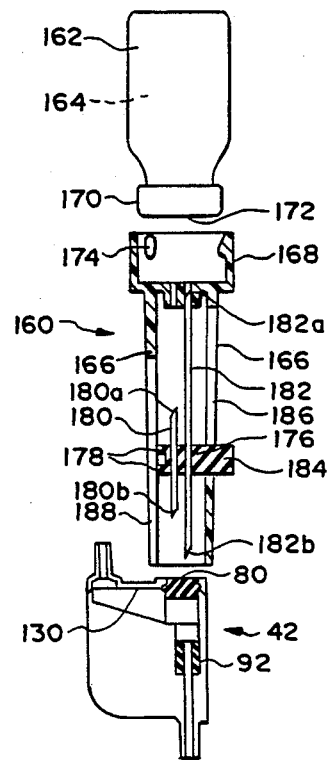
FIG. 12A is an exploded, partially cross-sectional view of the receptacle and an alternate embodiment of the cartridge.

Referring now to FIG. 12, there is illustrated in FIG. 12A an adapter 160 for connecting a chamber such as a standard drug vial 162 having a beneficial agent 164 therein to a receptacle 42. The adapter 160 includes a hollow rigid shell 166 with an enlarged vial end 168 for a snap fit engagement with the mouth 170 of the vial 162. The vial 162 includes a pierceable rubber stopper 172 therein. The enlarged vial end 168 may include projections 174. A reconstitution device showing a similar snap fit arrangement is disclosed in now allowed U.S. patent application Ser. No. 642,908 to William R. Aalto et al. filed on Aug. 21, 1984. The adapter 160 includes a sliding plate 176 slidably mounted within the hollow rigid shell 166. The sliding plate 176 may be of a preferably resilient material which may be slid along the longitudinal wall of the shell 166. The sliding plate 176 may include projections 178 slidably received within recesses in the shell wall. The resilient material and the projections 178 are intended to keep the sliding plate 176 stationary until movement is intended.

Mounted within the sliding plate 176 is a first hollow cannula 180 having a first pointed hollow end 180a facing the enlarged vial end 168 and a hollow pointed end 180b facing opposite the enlarged end 168. Also mounted within the sliding plate 176 is a second hollow cannula 182 including a hollow pointed first end 182a facing the enlarged end 168 and a second hollow pointed end 182b facing opposite the enlarged end 168. The sliding plate 176 includes a handle portion 184 projecting out of the shell 166 at a handle receiving slot 186 within the shell wall. The rigid shell 166 also includes a receptacle-receiving slot 188 for mounting about the bridge 130 of the receptacle 42.

The first hollow cannula 180 comprises an inlet flow path means into the drug vial 162 or other chamber. The second hollow cannula 182 comprises a separate outlet flow path out of the drug vial 162. The first ends 180a and 182a of the cannulas 180, 182 comprise chamber piercing means for piercing the rubber stopper 172 of the drug vial 162. The second ends 180b, 182b of the cannulas comprise receptacle piercing means.

In operation, the nurse or other medical personnel snaps the drug vial 162 within the enlarged end portion 168 of the adapter 160. The operator then grabs the handle portion 184 and moves it within the slot 186, thereby sliding the sliding plate 176 and the needles mounted therein toward the drug vial 162, piercing the rubber stopper 172 with both the first and second cannulas 180, 182. The adapter 160 is then mounted about the receptacle 42 with the shell 166 fitting thereabout and with the first and second cannulas 180, 182 piercing the pierceable situs 80, with the second cannula 182 engaging the bushing 92.

Figure 12B:
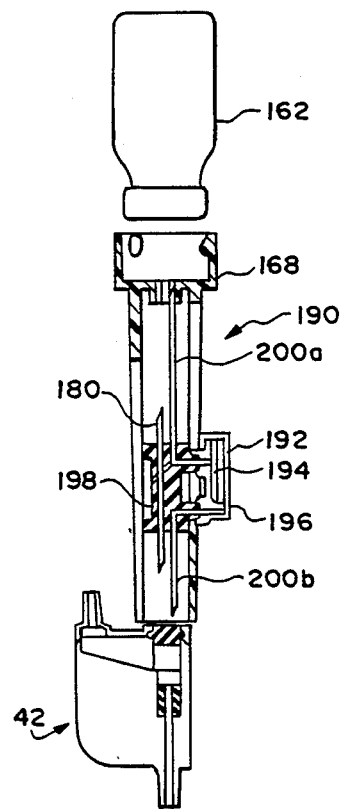
FIG. 12B is an exploded view of the receptacle and yet another alternate embodiment of the cartridge.

Referring now to FIG. 12B, there is shown an alternative embodiment of the adapter 190 similar to the adapter 160 shown in FIG. 12A. Here however the handle portion 196 that extends from the sliding plate 198 includes an air vent 192 such as a bacteria blocking hydrophobic membrane and a sterilizing 0.22 micron membrane filter 194. The second hollow cannula 200 is formed by two separate segments, segment 200a facing the enlarged adapter end portion 168 and segment 200b facing away from the adapter end portion 168. The segments 200a, 200b are in open communication through the interior of the handle portion 196, across the filter 194. Operation of the adapter 190 is the same as operation of the adapter 160, except that inclusion of the air vent 192 provides an exhaust for air within the drug vial 162 during priming. Also, the particulate matter barrier 194 is mounted within the adapter 190, preventing particulate matter from going downstream to the patient.

Figure 22:
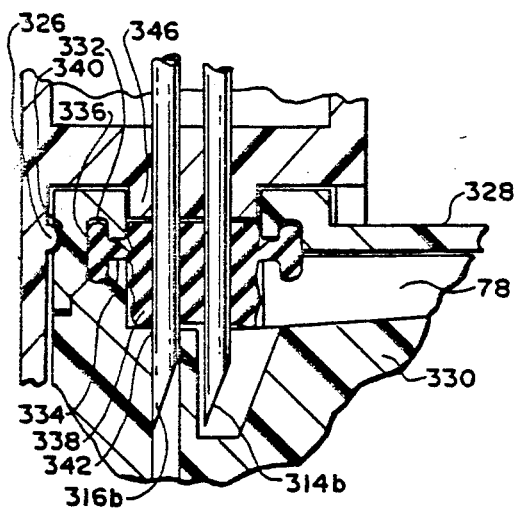
FIG. 22 is a fragmentary, cross-sectional view of the cartridge and receptacle illustrated in FIG. 21, with the piston-like injection site having been moved to its second, stressed position by full engagement of the cartridge and receptacle.
Figure 21:
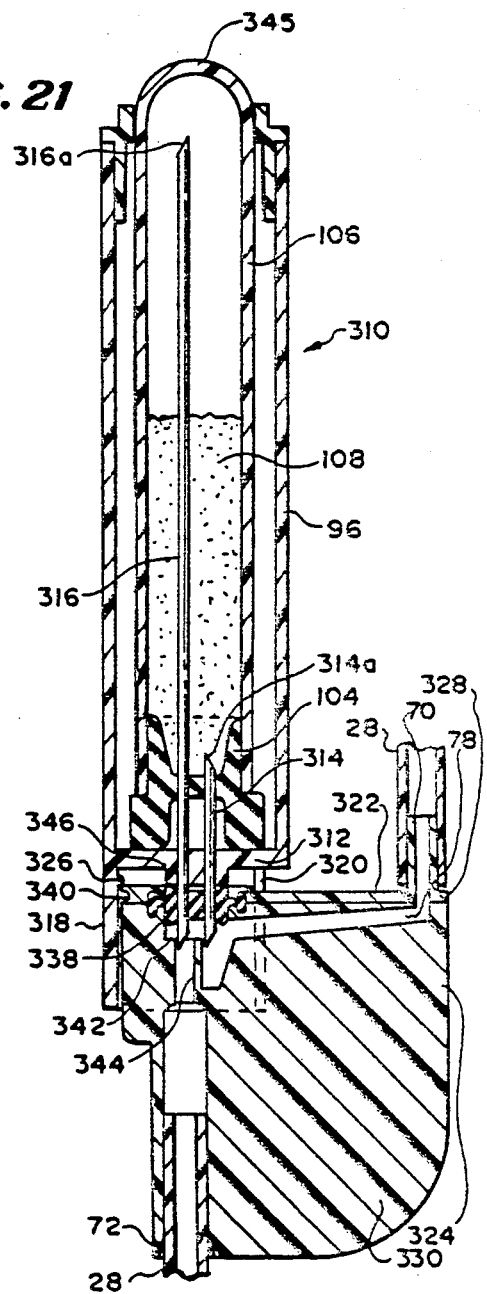
FIG. 21 is a longitudinal cross-sectional view of a cartridge as being inserted into a receptacle having a piston-like injection site.

Referring now to FIGS. 21 and 22, there is illustrated a cartridge 310 including a rigid cylinder 96 in which is slidably disposed a tubular chamber 106 having beneficial agent 108 therein. A base plate 312 extends across the cylinder 96. Disposed within the base plate 312 are first and second hollow cannulas 314, 316 respectively, each including a first pointed hollow end 314a, 316a respectively facing the tubular chamber 106. As with the cartridge 44, the tubular chamber 106 of the cartridge 310 slides from a first position out of engagement with the first and second cannulas to a second position illustrated in FIG. 21 where the first ends 314a, 316a of the first and second cannulas 314, 316 have pierced the rubber stopper 104 of the tubular chamber 106.

The cartridge 310 includes a keyway wall 318 extending from the side of the base plate 312 opposite the tubular chamber 106. A keyway slot 320 is defined within the keyway wall 318 for fitting about the bridge 322 of a receptacle 324. The keyway wall 318 includes one or more internal projections 326.

Unlike the cartridge 44, the second pointed hollow ends 314b, 316b of the first and second hollow cannulas 314, 316 respectively may extend the same distance from the base plate 312.

The receptacle 324 includes a receptacle inlet 70 and a receptacle outlet 72 connected to a fluid conduit 28 of an administration set such as the administration set 20. The receptacle 324 includes a fluid receiving segment 78 having an upstream end in fluid communication with the inlet 70 and a downstream end in fluid communication with the outlet 72.

The receptacle 324 does not include a bushing such as the bushing 92 in the receptacle 42; however, as will be described below in greater detail, once the cartridge 310 and the receptacle 324 are fully engaged, all liquid flowing through the receptacle must first pass through the tubular chamber 106, as is the case with the cartridge 44 and receptacle 42 described above.

The receptacle 324 includes upper and lower fitments 328, 330 defining an annular channel 332 substantially corresponding to and receiving the ring-like extension 334, including the enlarged periphery 336 thereof, of a pierceable, piston-like injection site 338 made of a resilient pierceable material such as polyisoprene. One or more detents 340 are provided about the exterior of the receptacle 324 for engagement with the internal projections 326 on the keyway wall 318.

An outflow seal 342 may be molded within the lower fitment 330 of the same relatively rigid plastic material as the remainder of the lower fitment 330. The outflow seal 342 defines an outflow channel 344 of larger diameter than the second hollow cannula 316 of the cartridge 310.

In operation, the nurse or other operator pushes down on the top 345 of the tubular chamber 106, sliding it from the first position to the second position illustrated in FIG. 21 where the stopper 104 abuts the base plate 312. The operator then mounts the cartridge 310 about the receptacle 324 in the only manner permitted by the keyway wall 318, keyway slot 320 and bridge 322. As illustrated in FIG. 21, the cannulas 314, 316 both pierce the situs 338. However, as illustrated in FIG. 21, the cartridge 310 is not fully mounted about the receptacle 324. In FIG. 21, the situs 338 is still in its normal position. Liquid flowing into the inlet 70 may flow through the outlet 72 by passing around the outflow seal 342, without entering the chamber 106.

To completely engage the cartridge and the receptacle, the nurse or other operator pushes down further on the rigid cylinder 96 to reach the fully engaged position illustrated in FIG. 22. By exerting downward pressure on the cartridge 310 relative to the receptacle 324, a central raised portion 346 pushes down on the situs 338 causing it to shift downwardly from its normal position illustrated in FIG. 21 to its second, stressed position illustrated in FIG. 22. The situs moves in a direction substantially mutually orthogonal to the ring-like extension of the situs. In the stressed position shown in FIG. 22, the situs 338 seals about the outflow seal 342 of the receptacle. The stressed position of the injection site 338 is maintained by the interfitment of the now-engaged projections 326 and detents 340.

Liquid now flowing into the inlet 70 and fluid receiving segment 78 is necessarily diverted into the first hollow cannula 314 through end 314b and into the chamber 106 containing the beneficial agent 108. The pressure upon the situs 338 causes an effective liquid seal between the situs 338 and the outflow seal 342. Liquid exits the tubular chamber 106 through the second cannula 316 and subsequently flows out of the receptacle through the inlet 72, downstream to the patient.

The cartridge 310 and receptacle 324 combination eliminate the need for the manufacture and assembly of the bushing to create a single flow path once the cartridge is engaged about the receptacle. After the beneficial agent has been delivered to the patient, the operator may remove the cartridge, whereupon the situs 338 returns to its normal position illustrated in FIG. 21, so that liquid may flow directly through the receptacle. Subsequent cartridges 310 may be secured through the receptacle 324, at which time the situs is once more forced into the stressed position shown in FIG. 22.

Figure 13:
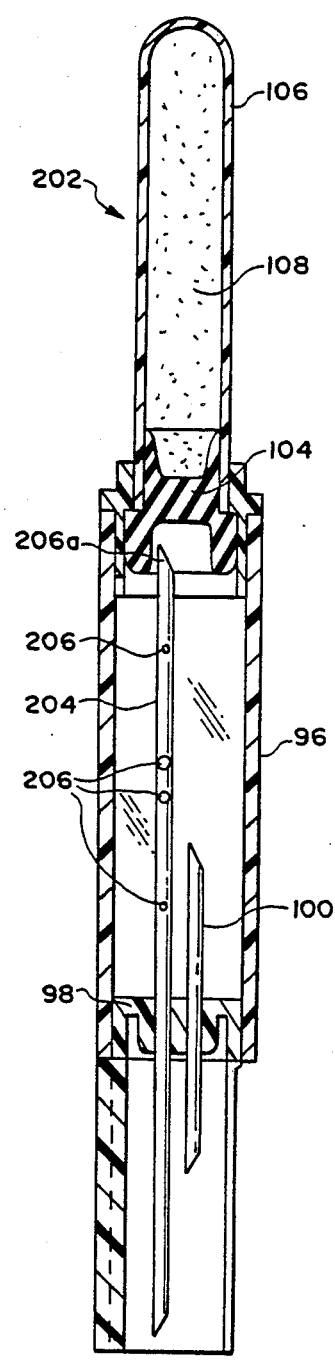
FIG. 13 is a cross-sectional view of a cartridge including a plurality of orifices in the sidewall of the second flow path means.
Figure 14:
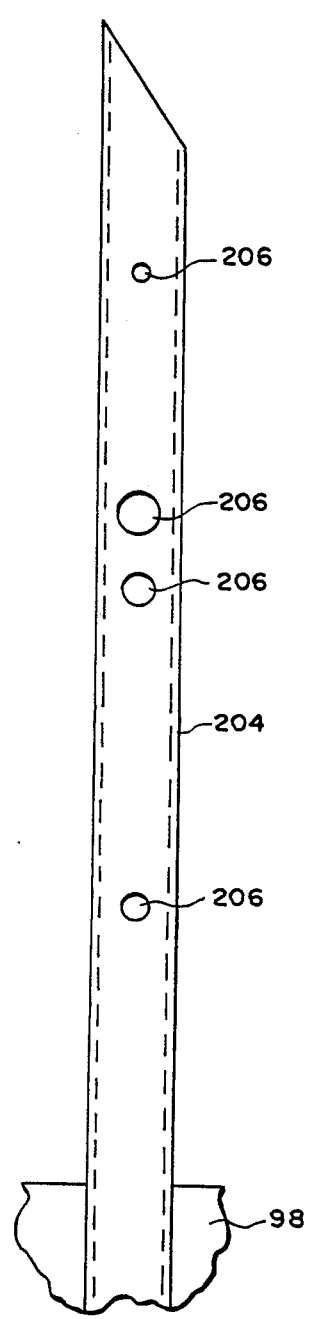
FIG. 14 is an enlarged side elevational view of a portion of the second flow path means illustrated in FIG. 13.

Referring now to FIGS. 13 and 14, there is shown a cartridge 202 wherein like elements are referred to by like reference numerals. The cartridge 202 includes a tubular chamber 106 and a rigid cylinder 96.

Here, the second hollow cannula 204 includes at least one and preferably a plurality of orifices 206 within the cannula, below the pointed first end 206a and above the base plate 98. The orifices may be created by use of a laser. With a given size cartridge 202, varying the number, placement and size of orifices 206 will vary the concentration of beneficial agent to be delivered with a medical liquid 22 to the patient. Depending upon the number, size and placement of the orifices, a particular defined concentration profile of drug in the liquid is created. As liquid enters the chamber 106 from the first cannula 100, the liquid level rises therein. As with the cartridge 44, a concentration gradient occurs along the height of the chamber 106, with concentration of the drug or other agent being greatest near the stopper 104 and least near the first end 206a of the second cannula. By means of the various orifices 206, several concentration strata may be permitted to exit the chamber 106. The exit orifice 206 size and spacing determines when the next level of concentration stratum exits the cartridge. While it is believed that the cartridge of the invention as disclosed within the present specification works quite well without these orifices 206, the use of the orifices 206 should be useful with certain, more hard to deliver drugs.

The amount of beneficial agent delivered downstream to the patient in a given unit of time may be expressed by the following equation:

$$DD = C_1Q_1 + C_2Q_2 \ldots C_NQ_N; \text{ where}$$

DD equals the amount of drug delivered to the patient per unit time, $C_N$ equals the concentration of drug in fluid level of stratum N and $Q_N$ equals the volume of liquid flowing through the orifice 206 in liquid level or stratum N in a given period of time.

$Q_N$ for a particular orifice depends upon the size of that orifice as well as the number and sizes of orifices at a lower elevation in the cannula 206 and the liquid flow rate through the administration set. Each orifice 206 may have an identical orifice directly opposite it on the cannula 206. If the maximum outflow rate permitted by an orifice or orifices 206 at a given elevation or below are less than the liquid flow rate into the chamber 106, liquid will rise to the next higher orifice 206 within the chamber.

Turning now to FIGS. 15 through 20 and with particular reference to FIGS. 15 through 17, there is disclosed a cartridge 208 for introducing a beneficial agent into a fluid conduit. The cartridge 208 includes a wall 210 defining a chamber 212 having a beneficial agent 214 therein. The cartridge wall 210 may be a glass drug vial including a body portion 216 and a neck portion 218 having an open end defining a mouth 220. A pierceable closure means such as pierceable stopper 222 is mounted within the mouth 220 and neck 218 of the cartridge 208. The stopper 222 includes an outer face 224 facing the chamber exterior and an inner face 226 facing the defined chamber 212.

The pierceable stopper 222 may include an outer lid portion 228 and a narrower plug portion 230. The lid portion 228 abuts the end of the mouth 220 and the plug portion 230 extends into the neck portion 218 of the chamber 212.

A chimney-like projection 232 extends from the inner face 226 in a direction substantially parallel to the length of the cartridge or, stated differently, in a direction substantially perpendicular to the lid portion 228 of the pierceable stopper 222. The chimney 232, the plug portion 230 and the lid portion 228 may be formed of a single piece of material, such as polyisoprene.

The closure means, in this case the pierceable stopper 222, is adapted to be pierced both at a point in alignment with the interior 234 of the chimney 232 and at a point in alignment with the area of the inner face 226 and external to the chimney 232. These two points are marked by reference numerals 236 and 238 respectively.

In the preferred embodiment, the cartridge further includes a flow connector 240 adapted for mounting about the mouth 220 and closure means of the cartridge. The flow connector includes cartridge connection means such as a sleeve 242 having an enlarged channel 244 at one end thereof for tight interfitment with the mouth 220 and the pierceable stopper 222.

The flow connector 240 further includes a base 246 mounted to the other end 248 of the sleeve 242. It is preferred that the base 246 is rotatably mounted within the sleeve 242.

The flow connector 240 includes first and second cannulas 250, 252 mounted within the base 246. The first and second cannulas include first pointed ends 250a, 252a respectively facing the pierceable stopper. Similarly, the cannulas each include a second pointed end 250b, 252b extending away from the pierceable stopper on the opposite side of the base 246. The cannulas extend in a direction substantially parallel to the length of the chimney 232 and substantially perpendicular to the lid portion 228 of the pierceable stopper 222.

The flow connector further includes a projecting key 254 extending from the stopper facing side of the base 246. A mating keyway 256 is disposed within the outer face 224 of the stopper 222. The location of the key 254 and keyway 256 may of course be reversed. The key and keyway may have an arc design defined by a radius having a center in alignment with the center of the base 246.

The first ends 250a, 252a of the cannulas extend substantially the same distance from the chamber facing side of the base 246. In the preferred embodiment, the second ends 250b, 252b of the cannulas are disposed such that the second cannula second end 252b extends from the chamber distant side of the base further than the first cannula 250.

The base 246 includes an extension wall 258 extending from the chamber distant side thereof, surrounding and spaced from the first and second cannulas. The extension wall 258 includes a defined slot 260 therein. The extension wall 258 and the second ends 250b, 252b are covered with a cap 262 provided to prevent harm to the nurse or other operator and to prevent touch contamination of the cannulas.

The slot 260 within the extension wall 258 serves as a keyway means for enabling proper engagement of the cartridge 208 with a receptacle such as receptacle 42 mounted in the fluid conduit 28 of an administration set 20.

In operation, the nurse or other operator removes the cap 262 from the extension wall 258 and rotates the extension wall until the key 254 and keyway 256 mate, at which time the extension wall 258 and base 246 are urged toward the pierceable stopper, until the hollow cannulas are moved from a first position illustrated in FIG. 16 in which they are spaced from the chamber 212, to a second position illustrated in FIG. 17 in which both the first and second cannulas 250, 252 have pierced the closure means and are in flow communication with the chamber 212. In the second position, the first cannula pierces the inner face 226 of the stopper at a point external to the chimney. The second cannula pierces the stopper so as to have its first end 252a disposed within the chimney 232.

The cartridge 208 is then inserted about the receptacle 42 illustrated in FIG. 1 by mounting the slot 260 over the bridge 130 of the receptacle 42. In this position, the first and second cannulas 250, 252 will be disposed within the receptacle in the same manner as first and second cannulas 100, 102 illustrated in FIG. 9. Liquid flowing into the receptacle will flow into the chamber 212 through the first cannula 250 and mix with the beneficial agent 214 therein. When the liquid rises to the level of the top 264 of the chimney 232, liquid will flow down the chimney 232 through the second cannula 252 and bushing 92 to the patient. Alternatively, the lengths of the cannulas 250, 252 on the stopper distant side of the base 246 can be changed so that the cartridge 208 may be used with the receptacle 324 illustrated in FIGS. 21 and 22.

Referring to FIGS. 18 through 20, there is disclosed yet another cartridge 266 including a wall 268 relatively impermeable to vapor and air and a pierceable closure means such as pierceable stopper 270 which together define a chamber 272. The pierceable stopper 270 includes an outer face 276, and inner face 278 facing the chamber 272.

A chimney 280 extends from the inner face 278 in a direction substantially parallel to the length of the cartridge or, stated differently, in a direction substantially perpendicular to the outer face 276. A beneficial agent 282 is stored within the chamber within the chimney 280 itself. A liquid pervious barrier 284 such as a particulate matter barrier having a nominal pore size no greater than about 20 microns, such as a nylon mesh screen, is mounted at the top 286 of the chimney 280. The liquid pervious barrier 284 retains the beneficial agent 282 within the chimney 280 until such time as the cartridge 266 is plugged into the adapter 42.

The cartridge 266 in the preferred embodiment also includes a flow connector 288 having a base 290. The base 290 includes a chamber distant side 292 and a chamber facing side 294. Mounted within the base 290 are first and second cannulas 296, 298 respectively. An extension wall 300 extends from the chamber distant side 292 of the base 290 and defines a slot 302 enabling mounting of the cartridge 266 upon a receptacle 42 in the manner described above relative to other cartridges.

The first pointed end 296a of the first cannula 296 extends from the base 290 a shorter distance than the first end 298a of the second hollow cannula 298. Similarly, the second pointed end 296b of the first hollow cannula extends from the chamber distant side of the base 290 a shorter distance than the second hollow end 298b of the second cannula 298, for use with the cartridge 44 described above. The disposition of the second hollow cannula ends 296b, 298b may be changed for use with a receptacle such as the receptacle 324 illustrated in FIG. 21.

In use, the operator urges the first and second cannulas 296, 298 through the pierceable stopper 270, until the chamber facing side 294 of the base abuts the stopper 270, as illustrated in FIG. 19. Unlike the embodiment of FIGS. 15 through 17, however, where the second cannula is disposed within the chimney, in the embodiment illustrated in FIGS. 18 through 20 it is the first cannula 296 which is disposed within the chimney 280. Because the beneficial agent is retained within the chimney, an upward flow path of liquid mixing with beneficial agent is created within the chimney itself.

Eventually liquid reaches the liquid pervious barrier 284 and flows down the outside wall of the chimney 280. The liquid, with the beneficial agent therein, collects within the chamber 272 outside the chimney 280. The liquid level rises until it reaches the level of the first end 298a of the second cannula 298, at which time liquid flows into the second cannula 298 and downstream to the patient. The mounting of the cartridge 266, including the flow connector 288 about a receptacle 42 is illustrated in FIG. 20.

While several embodiments and features have been described in detail herein and shown in the accompanying drawings, it will be evident that various further modifications are possible without departing from the scope of the claimed invention.

What is claimed:

1. A cartridge for introducing a beneficial agent into a fluid conduit comprising:
   (a) a wall defining chamber for containing a beneficial agent; and
   (b) pierceable closure means closing said chamber, said pierceable closure means including an outer face and an opposed inner face facing the defined chamber, said closure means further including a hollow, open ended protrusion extending from said inner face in a direction substantially parallel to the length of said cartridge, wherein said beneficial agent is disposed within said hollow protrusion and wherein said beneficial agent is retained within said hollow protrusion by means of a liquid pervious barrier.

2. The cartridge in accordance with claim 1, wherein said pierceable closure means comprises a pierceable stopper mounted within a mount of said defined chamber.

3. The cartridge in accordance with claim 1, wherein said liquid pervious barrier comprises a particular matter barrier.

4. The cartridge in accordance with claim 3, wherein said particulate matter barrier has a nominal pore size no larger than about 20 microns.

5. The cartridge in accordance with claim 3, wherein said particulate matter barrier has a nominal pore size of no greater than about 10 microns.

6. The cartridge as in claim 1, wherein said closure means is adapted to be pierced both at a point in alignment with the interior of said hollow protrusion and at a point in alignment with the area of said inner face external to said hollow protrusion.

7. The cartridge in accordance with claim 6, further comprising a flow connector adapted for mounting to the chamber, said flow connector including
   (a) a base and
   (b) two hollow cannulas, each pointed at each end, mounted within the base and extending in a direction substantially parallel to said hollow protrusion, said hollow cannulas being adapted to pierce the pierceable closure means, such that said first cannula pierces said closure means in alignment with said hollow protrusion and such that said second cannula pierces said closure means at a point on said closure means inner face external to said hollow protrusion.

8. The cartridge as in claim 7, said base including a chamber distant side, wherein said second cannula extends from said chamber distant side of said base further than said first cannula.

9. The cartridge as in claim 7, further comprising a chamber facing side of said base, said second cannula extending from said chamber facing side of said base farther than said first cannula.

10. The cartridge as in claim 7, further comprising a chamber facing side of said base, said first and second cannulas extending substantially the same distance from said chamber facing side.

11. The cartridge as in claim 7, said base including a chamber distant side, further comprising a cap sealingly mounted over said portions of said cannulas extending from said chamber distant side of said base.

12. The cartridge as in claim 7, further comprising one of a key and a keyway disposed on said outer face of said closure means and the other of said key and keyway mounted upon said base, wherein said base is rotatable relative to said pierceable closure means and wherein said first cannula is in alignment with said hollow protrusion when said key and said keyway are engaged.

13. The cartridge as in claim 12, further comprising receptacle keyway means extending from said chamber opposite side of said base, for proper engagement with a receptacle mounted in the fluid conduit of an administration set.

* * * * *

UNITED STATES PATENT AND TRADEMARK OFFICE
CERTIFICATE OF CORRECTION

PATENT NO. : 4,936,829

DATED : June 26, 1990

INVENTOR(S) : Brian D. Zdeb, William E. Younkes, Thomas J. Roeser

It is certified that error appears in the above-identified patent and that said Letters Patent is hereby corrected as shown below:

In column 21, at line 46, delete "defining chamber" and substitute --defining a chamber-- therefor.

In column 22, at line 1, delete "mount" and substitute --mouth-- therefor.

In column 22, at line 4, delete "particular" and substitute --particulate-- therefor.

Signed and Sealed this

Second Day of July, 1991

Attest:

HARRY F. MANBECK, JR.

Attesting Officer

Commissioner of Patents and Trademarks